United States Patent [19]

Spoon et al.

[11] Patent Number: 4,949,732

[45] Date of Patent: Aug. 21, 1990

[54] APPARATUS FOR INSERTION AND FIXATION OF AN INTRA UTERINE CONTRACEPTIVE DEVICE TO THE UTERINE FUNDUS

[75] Inventors: Herbert Spoon, Bridgewater; Vincent Vaillancourt, Livingston, both of N.J.; Robert Caspari, W. Nyack, N.Y.

[73] Assignee: Gyno Pharma Inc., Somerville, N.J.

[21] Appl. No.: 397,861

[22] Filed: Aug. 24, 1989

[51] Int. Cl.⁵ .................................................. A61F 6/00
[52] U.S. Cl. ..................................... 128/839; 128/840
[58] Field of Search .............................. 128/833–841, 128/783, 775, 784, 788; 604/891

[56] References Cited

U.S. PATENT DOCUMENTS

| | | | |
|---|---|---|---|
| 2,008,526 | 7/1935 | Wappler | 128/788 |
| 3,635,215 | 1/1972 | Shea | 128/840 |
| 3,763,856 | 10/1973 | Blomberg | 128/840 |
| 3,771,520 | 11/1973 | Lerner | 128/840 |
| 3,783,861 | 1/1974 | Abramson | 128/840 |
| 3,794,025 | 2/1974 | Lerner | 128/840 |
| 4,143,656 | 3/1979 | Holmes | 128/840 |
| 4,418,686 | 12/1983 | Child | 128/833 |
| 4,708,134 | 11/1987 | Wildemeersch | 128/840 |
| 4,721,105 | 1/1988 | Wildemeersch | 128/840 |

Primary Examiner—Robert A. Hafer
Assistant Examiner—Michael A. Brown
Attorney, Agent, or Firm—Louis S. Gillow

[57] ABSTRACT

A one-hand apparatus for insertion and fixation of an IUD which has a penetration member with a needle at the distal end for holding an attaching member of an IUD. The penetration member with the IUD are slidably received and positively locked within an insertion tube to prevent slidable movement of the needle during initial insertion to touching contact of the insertion tube with the fundus. Thereupon, the penetration member is released by thumb action of the user upon a lock-/release member to allow penetration of the needle into the fundus by a predetermined distance to fix the IUD to the fundus.

9 Claims, 5 Drawing Sheets

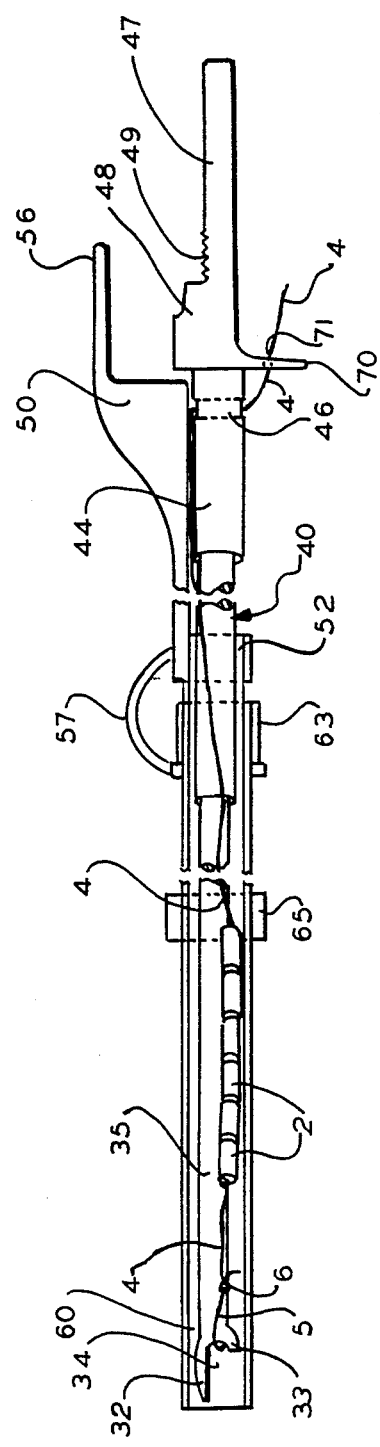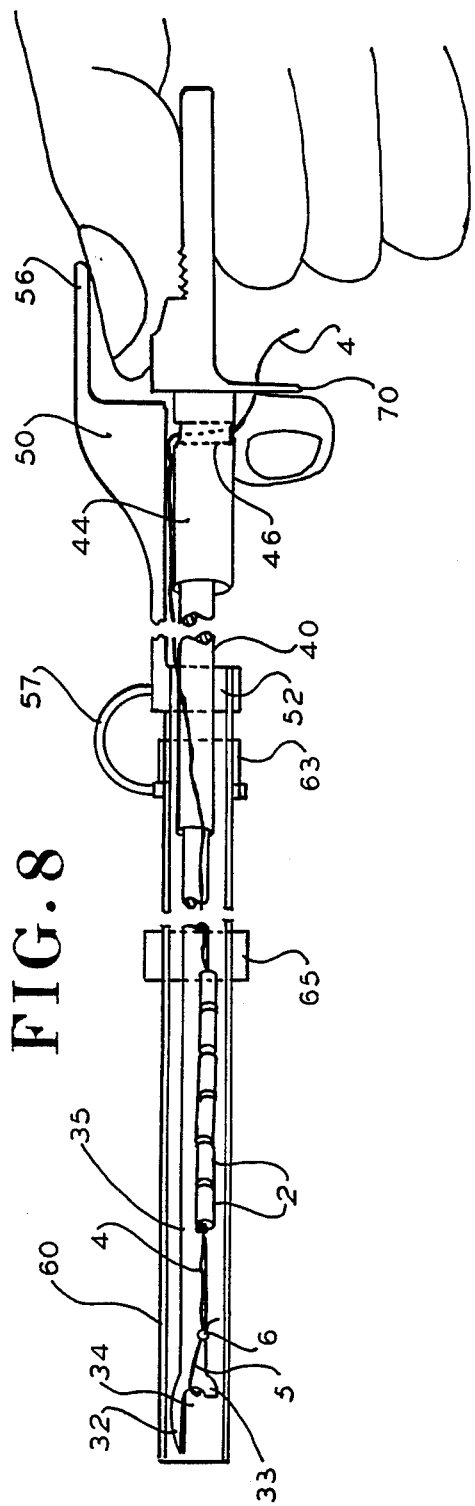

APPARATUS FOR INSERTION AND FIXATION OF AN INTRA UTERINE CONTRACEPTIVE DEVICE TO THE UTERINE FUNDUS

BACKGROUND OF THE INVENTION

The present invention relates to a one-hand apparatus for insertion and fixation of an intra uterine contraceptive device (IUD) to the uterine fundus.

The IUD is easily manipulated by the novel one-hand apparatus for its insertion and fixation to the fundus.

In the prior art, IUD insertion apparatus were complicated and required two hands for insertion and fixation. Because the user had to make many manipulations with both hands during insertion and fixation with prior art apparatus, they were complicated and awkward to use.

U.S. Pat. No. 4,721,105 discloses a device for the insertion and fixation of an IUD to the uterine fundus. The device comprises a thread affixded to the IUD and to a retaining member, a needle for the insertion of the retaining member attached to the thread into the uterine muscle, a protecting member for the needle, a receiving member for the IUD, an actuating member for the needle, movable with respect to the protecting member, and a locking member for temporarily locking the activating member to the protecting member. The structure of the '105 Patent presents difficulties to the user in that the device cannot be manipulated effectively with one-hand, which is especially desirable by the user in view of the necessity for concurrent manipulations by the other hand of the user. Also, the structure of the '105 Patent may not provide a secure locking both of the needle and of the protecting member, so as to prevent inadvertent exposure of the needle during insertion which can result in laceration of the uterine cavity.

SUMMARY OF THE INVENTION

In is an object of the present invention, therefore, to provide an improved one-hand IUD insertion and fixation apparatus.

The IUD used with the apparatus of the present invention can be formed of a series of hollow members connected into a flexible assembly by a thread passing through the longitudinal passage in each hollow member. The thread is formed with a loop and a knot at top for fixing to the fundus. The IUD is made of a material which is effective for the prevention of contraception.

The apparatus comprises a penetration member having a needle at the distal end for inserting the IUD in the fundal tissue, an insertion tube for slidably receiving the penetration member with the IUD, and a lock release member to positively secure the needle within the insertion tube and to releasably enable the needle to move in relation to the insertion tube, by which the needle penetrates and fixes the IUD in the fundal tissue.

These and other objects not enumerated are achieved by utilizing the novel one-hand IUD insertion and fixation apparatus of the present invention.

BRIEF DESCRIPTION OF THE DRAWINGS

A more complete understanding of the IUD and of the one-hand apparatus for insertion and fixation of the IUD to the-fundus may be had from the following detailed description thereof, particularly when read in the light of the accompanying drawings, wherein:

FIG. 7 is a side partially sectional view of the assembled apparatus and the IUD;

FIG. 8 is a side partially sectional view of the assembled apparatus and the IUD during insertion into the uterine cavity;

DETAILED DESCRIPTION OF THE PREFERRED EMBODIMENT

Figure 1:
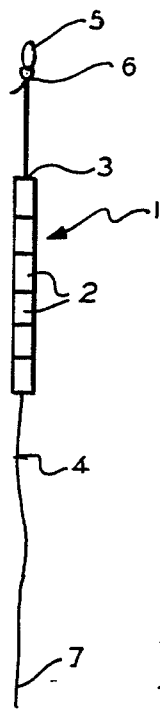
FIG. 1 is a side elevational view of the IUD of the present invention.

In the accompanying drawings all reference numerals refer to corresponding elements. The positions of the elements are relative to the applicator of the IUD.

An embodiment of an IUD which can be inserted by use of the apparatus of the present invention is shown in FIG. 1. The IUD, generally designated 1, is in the form of a stem made of a series of six hollow members or sleeves 2, made of copper which is effective as a contraceptive in the uterus. The hollow members 2 each have a longitudinal passage 3 therein with a thread 4 passing therethrough so as to connect each of the hollow members 2 to form a chain. Numbers 1 and 6 of the hollow members 2 are crimped inwardly onto the thread 4 so as to lock the flexible assembly together. At the top or distal end of the IUD 1 the distal end of the thread 4 forms a loop 5 which terminates in a knot 6. The loop 5 and the knot 6 constitute a fixation means after insertion in the fundal tissue. The proximal end of the thread 4 terminates in a thread end 7 for traction with the novel one-hand apparatus of the present invention. The hollow members 2 are loosely aligned and crimped onto the thread 4 so that the IUD is a flexible unit after being inserted and fixed to the fundal tissue. The contraceptive drug substance of the IUD consists of elemental copper in the form of the hollow sleeves 2 positioned on a length of monofilament polypropylene surgical suture thread 4. The surface area of the copper is about 330 mm².

The apparatus for insertion and fixation of the IUD of the present invention can best be described by reference to FIGS. 2-13. The novel apparatus for insertion and fixation of the IUD in accordance with the present invention is generally designated 20 and is comprised of a stainless steel needle 30, a needle holder/plunger penetration member 40, an insertion tube lock/release 50, and an insertion tube 60 including a cervical stop 65.

Figure 3:
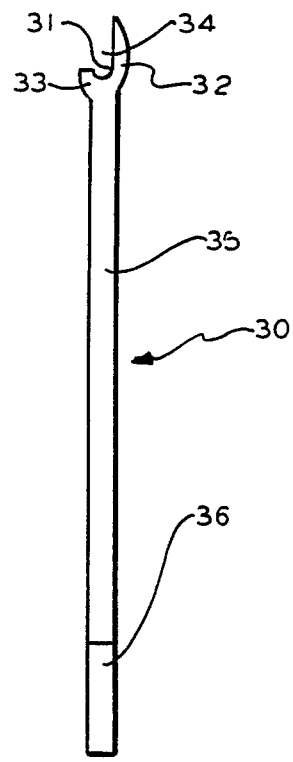
FIG. 3 is a side elevational view of the needle member of the apparatus.
Figure 4:
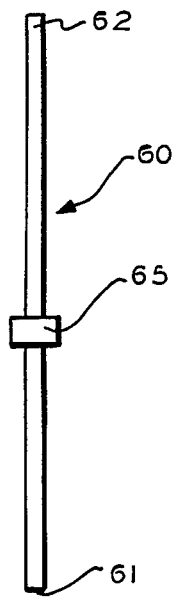
FIG. 4 is a side elevational view of the insertion tube member of the apparatus.
Figure 5:
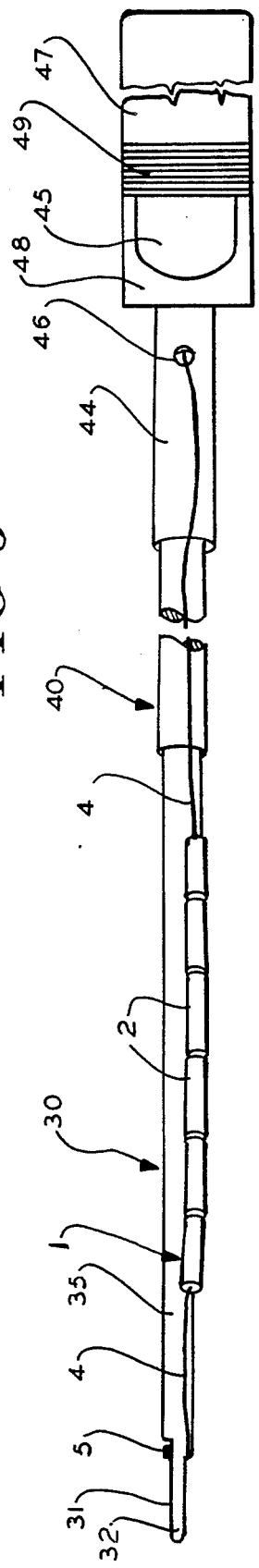
FIG. 5 is a top plan view of the plunger member of the apparatus with the IUD held thereon.
Figure 6:
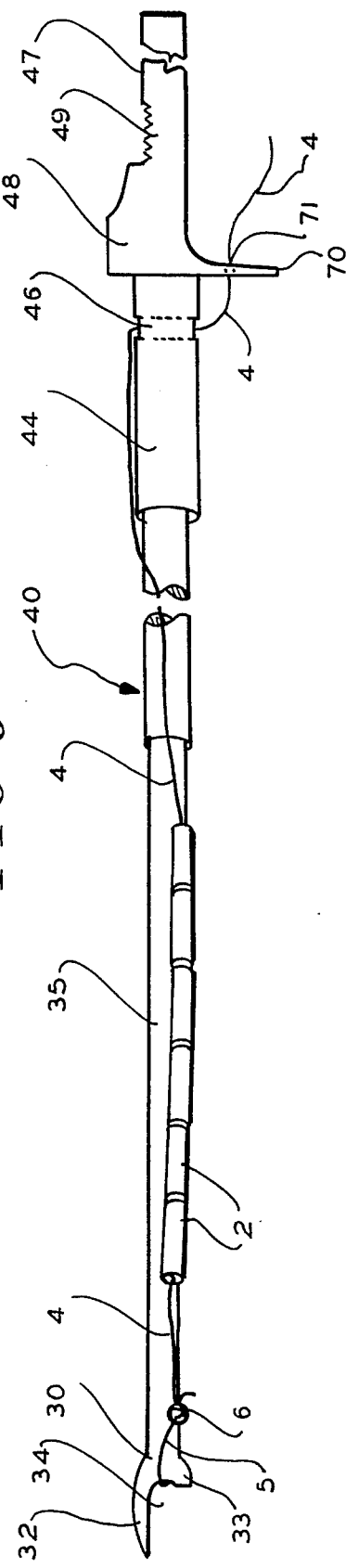
FIG. 6 is a side elevational view of the plunger member of the apparatus with the IUD held thereon.

Referring now to FIGS. 3 and 4 the stainless steel needle 30 has a long cylindrical shape, e.g. the length may be about 6.5 centimeters. The distal end of the needle 30 is an open hook 31 formed by a sharp elongated prong 32 and a shorter prong 33 with an open eye 34 between the prongs 32, 33 for placement of the loop 5 of the IUD 1 therebetween. When upright and ready for insertion and fixation to the uterine fundus the hollow sleeves 2 of the IUD 1 encircle and hang down along the shank 36 of the needle 30. The thread end 7 of the IUD 1 continues down along the shank 35 of the needle 30 and extends beyond the needle proximal end 36 which is joined to the needle holder/plunger, 40.

Figure 2:
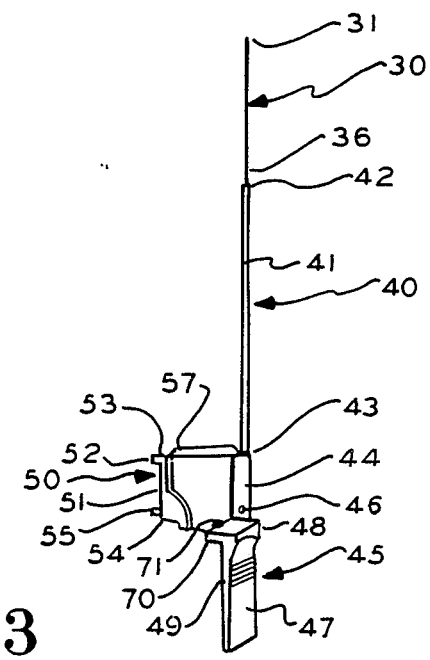
FIG. 2 is a side view of the plunger member of the one-hand apparatus of the present invention for insertion and fixation of the IUD to the fundus.

Referring now to FIG. 2 the penetration member 40, which can be formed from an acetyl copolymer material, includes a plunger 41. At the distal end 42 of the plunger 41 the needle end 36 is held. At the proximal end 43 of the penetration member 40 an enlarged diameter portion 44 continues toward the user and terminates in a thumb holder, 45. The enlarged portion 44 of the penetration member 40 has a hole 46 therethrough perpendicular to the axis of the plunger 41 and forward of the thumb holder 45. The thumbe holder 45 has a generally flat surface 47 parallel to the axis of the plunger 41. The flat surface 47 has a molded portion 48 adjacent to the enlarged portion 44 of the plunger 41. The molded portion has the general configuration for the thumb of a person using the apparatus for inserting the IUD 1. The flat portion 47 is provided with gripping ridges 48 to provide for positive engagement by the thumb of the user without slippage. Below the molded portion 48 and perpendicular to the plunger 41 is a forefinger stop 70 which has a generally flat configuration perpendicular to and forward of the molded portion 48. At the bottom of the forefinger stop 70 is a central notch 71 for the thread distal end 7 of the IUD 1.

Representative lengths for the plunger 41 and the enlarged portion 44 are 5.226 inches and 0.540 inches, respectively.

To position the IUD 1 for insertion, the loop 5 is placed within the hook 31; the thread end 7 of the IUD 1 extends down from the IUD 1 past the plunger 41 and through the hole 46 to the forefinger stop and central notch 71 wherein the thread end is held taut by the forefinger of the applicator.

Referring now to FIGS. 2-12 the penetration member 40 with the needle 30 holding the IUD 1 thereon are slidably covered by the insertion tube 60 which is slipped over the IUD 1 on the hook 31 of the needle 30 and down over the plunger 41. The insertion tube 60 may be made of high density polyethylene. The distal end 61 of the insertion tube 60 completely covers the needle 30 so that the hook 31 does not cut any uterine cavity tissue while the IUD 1 is being inserted into the fundus by the insertion apparatus 20. The insertion tube 60 is provided with a cervical stop 65 which is movably positioned by the user on the tube 60 at a measured distance between the distal end 61 and the cervical stop 65 corresponding to the distance between the outer cervical os and the fundus. The cervical stop limits the distal end 61 to touching contact with the fundus before penetration by the needle 30. The cerical stop 65 may be made of molded thermoplastic rubber.

Figure 9:
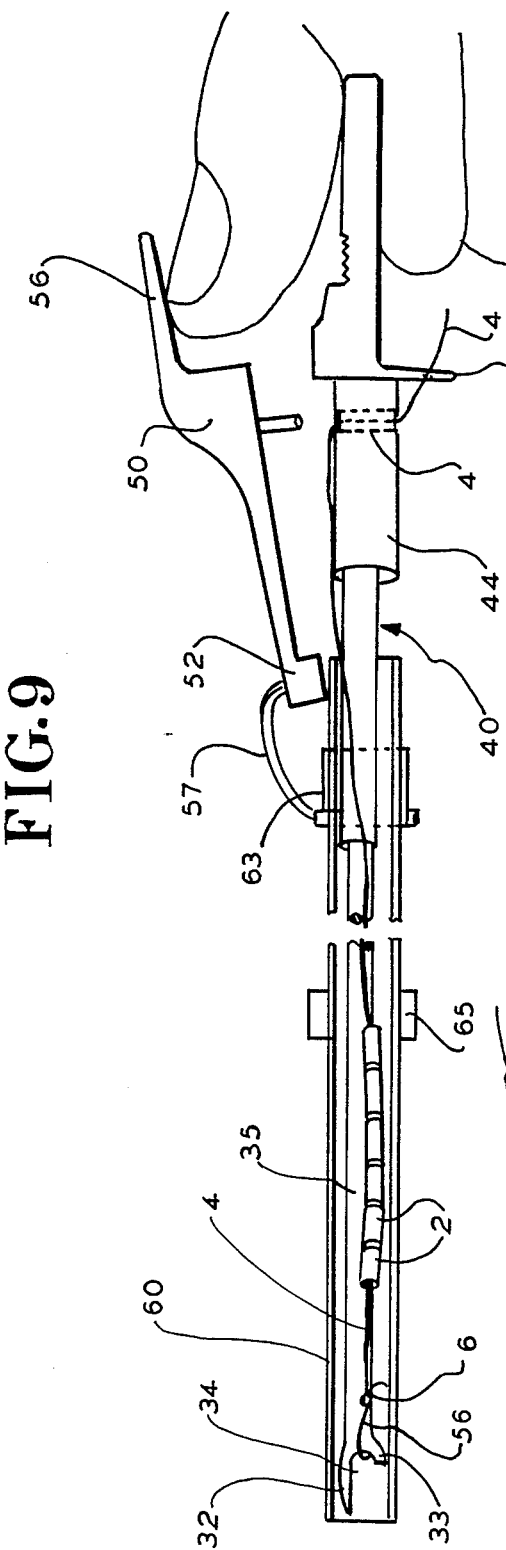
FIG. 9 is a side partially sectional view of the assembled apparatus and the IUD after insertion into the uterine cavity.
Figure 11:
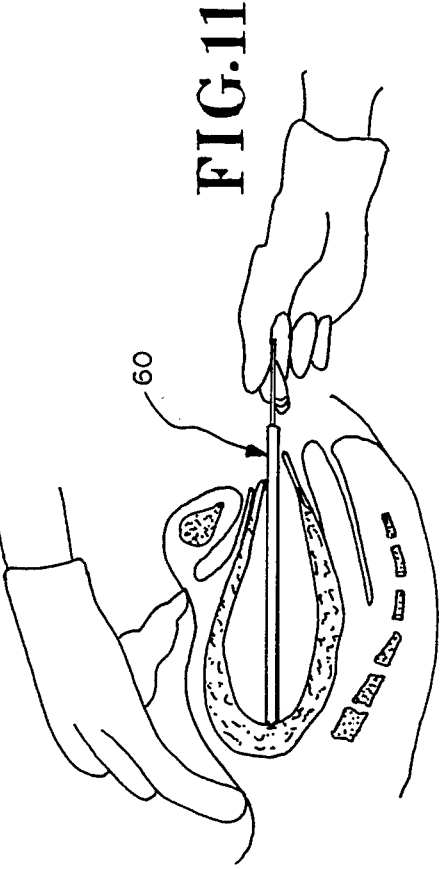
FIG. 11 is a side partially sectional schematic representation of the apparatus after insertion and fixation of the IUD to the fundus.
Figure 10:
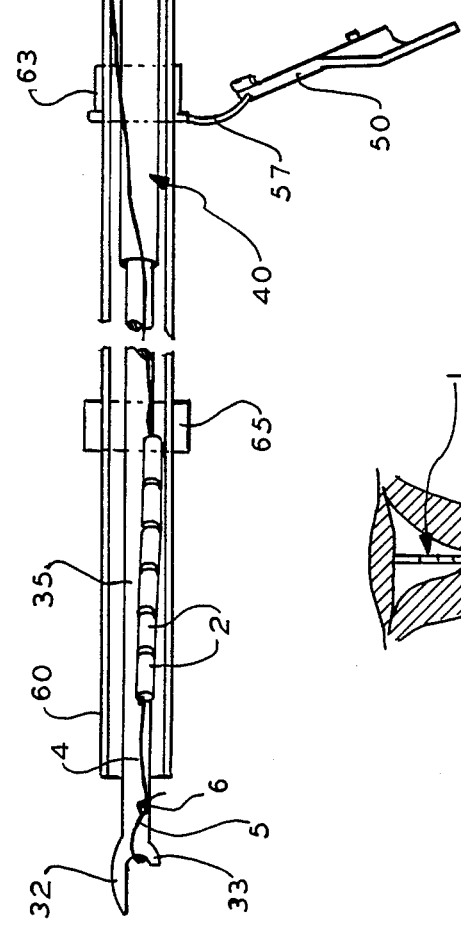
FIG. 10 is a side partially sectional view of the apparatus during fixation of the IUD to the fundus.

In order to limit the penetration depth of the needle 30 holding the IUD 1 into the fundal tissue, the proximal end 61 of the insertion tube 60 is spaced a predetermined distance apart from the thumb holder 45 by the lock/release 50; e.g., about one cm. The lock/release 50 may be made of molded acetyl polymer. The lock/release 50 is an elongated flat plastic spacer having a half sleeve 52 at the distal end 53. The half sleeve 52 slides over to firmly grip and lock the proximal end 61 of the insertion tube 60. The proximal end 54 of the lock/release 50 has an axially perpendicular lug 55 which engages in a locking frictional fit with the hole 46 of the penetration member 40 after the thread 4 of the IUD 1 is inserted and tightened through the hole 46. After the half sleeve 52 is in locking engagement with the proximal end 62 of the insertion tube 60, and the lug 55 is in locking engagement with the hole 46 of the penetration member 40, the insertion tube 60 completely covers and prevents slidable movement of the needle 30 within the insertion tube 60, which is now in position for insertion through the cervical canal to the uterine fundal. The lock/release 50 is provided with an extension 56 which projects toward the user to just above the thumb when placed in the holder 45. After the insertion apparatus 20 has been inserted through the cervical canal so that the distal end 62 of the insertion tube 60 touches the fundus, the applicator further extends his thumb away from and above the thumb holder 45 which moves the extension 56 of the lock/release 50 away from the penetration member 40 and the insertion tube 60 so that the half sleeve 52 and the lug 55 are released (see FIGS. and 8 and 9). Whereupon the lock/release 50 falls away from the insertion apparatus 20. The lock/release 50 is prevented from completely falling away by a tether clasp 57 attached to a retaining ring 63. After the lock/release 50 has been disengaged and has fallen away, the penetration member 40 is now released and is permitted to be further presed forward in slidable movement within the insertion tube 60 by the user so as to cause the needle to move forward from within the insertion tube 60 and to penetrate the fundal tissue by a distance which has been predetermined to be the effective distance of penetration into the fundus by the needle 30 so that the loop 5 and the knot 6 of the IUD 1 are inserted and fixed within the fundus tissue, e.g., a distance of about one cm. As shown in FIG. 9, the proximal end 61 of the insertion tube 60 is held by the lock/release 50 to separate the proximal end 61 of the insertion tube 60 from the distal end 80 of the enlarged portion 44 of the penetration member 40 for a distance of about one cm. At this position, the distal end 62 of the insertion tube 60 is in contact with the fundus. Also at this position, the distal end 62 of the insertion tube 60 fully covers and prevents contact of the sharp elevated prong 32 of the needle 30 with the fundus. As shown in FIG. 10, the thumb of the user has lifted the extension 56 and has caused the lock/release 50 to fall completely away from the penetration member 40 so that the half-sleeve 52 has been released from the proximal end 80 of the insertion tube 60 and the lug 55 has been released from the hole 46 of the penetration member 40. This now permits relative movement forward of the penetration member 40 within the insertion tube 60 by continuing forward pressure of the thumb of the user on the thumb holder 45. This forward relative movement of the penetration member 40 uncovers the sharp prong 32 from within the distal end 62 of the stationary insertion tube 60. Thereupon, the prong 32, with the loop 5 and the knot 6 of the IUD 1 thereon, now penetrates the fundus by a distance of about one cm. After penetration for about one cm the penetration member 40 is withdrawn from within the stationary insertion tube 60 and the IUD 1 is released from the prong 32. The loop 5 and the knot 6 of the IUD 1 are retained and fixed within the fundal tissue after the penetration member 40 has been completely withdrawn. Thereafter, the insertion tube 60 is also withdrawn from the uterine cavity so that the IUD 1 remain fixed to the fundal tissue to serve as an effective contraceptive.

The IUD together with the apparatus for insertion and fixation have great advantages. During manufacture, the IUD 1 is put on the needle 30 by interlocking the loop 5 with the hook 31. Thereafter, the thread end 70 is pulled downward and through the hole 46 of the penetration member 40, and centered by the central notch 71 of the forefinger stop 70. Thereafter the half sleeve 52 is slipped over the insertion tube 60 and the projection 55 is frictionally engaged within the hole 46 so as to maintain the insertion tube 60 completely over the needle 30 and the IUD 1. This completes the assembly of the IUD 1 with the apparatus for insertion and fixation 20 by a user. The user need only use one hand with the apparatus 20 to complete the insertion and fixation of the IUD 1. This permits the user to use his other hand; for example, to handle a cervical canal shounder and/or other devices or manipulations required during skilled inserted and fixation of the IUD of the present invention.

Figure 13:
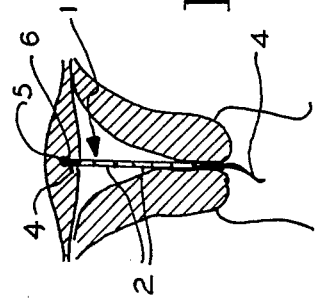
FIG. 13 is a top partially sectional schematic representation of the IUD after insertion and fixation to the fundus.
Figure 12:
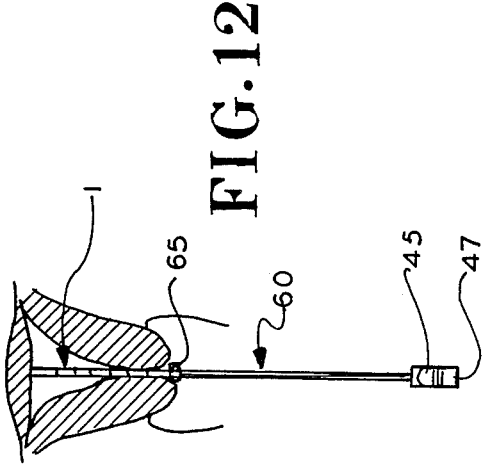
FIG. 12 is a top partially sectional schematic representation of the apparatus after insertion and fixation of the IUD to the fundus.

The IUD 1 of the present invention is of sufficient length, of about 6 copper sleeves to extend from the fundus into the uterine cavity as shown in FIG. 13. This allows copper action in this portion of the uterus as an effective contraceptive.

As can be seen from the foregoing, the one-hand apparatus 20 of the present invention provide for the effective insertion and fixation in the fundal tissue, and constitute an improvement over known techniques.

Although the apparatus has been described with reference to a particular IUD formed of copper sleeves, the invention is not limited to use with such an IUD. Similarly, although preferred dimensions and material have been described the invention is not limited thereto.

While the present invention has been described with a degree of particularity in connection with a preferred embodiment, it should be understood that variations and modifications will be obvious to those skilled in the art without departing from the scope of the present invention as defined in the appended claims.

What is claimed is:

1. A one hand apparatus for inserting and fixing an intra uterine contraceptive device (IUD) having an attaching means for fixation to the fundus; said apparatus comprising:
    a penetration member having a holding means for a digit of a user at the proximal end thereof and a needle at the distal and thereof, said needle adapted to engage said attaching means of said IUD whereby penetration of said needle by a predetermined distance into the fundus causes fixation of said IUD to the fundus;
    an insertion tube for insertion into the uterine cavity and for slidably receiving said penetration member with said IUD within said insertion tube;
    a lock/release member for positively locking said insertion tube to said penetration member with said penetration member in said insertion tube to prevent slidable movement of said penetration member during insertion of said insertion tube into the uterine cavity by movement of one hand of the user on said holding means, and for thereafter releasing, with the sane hand of the user, said penetration member from said insertion tube to permit slidable movement of said needle forward from within said insertion tube by said predetermined distance of penetration into the fundus by the slidable movement of said needle forward from within said insertion tube;
    said lock/release member including a clamping means at one end for positively locking said insertion tube to said lock/release member;
    said lock/release member also including a locking means at the other end for positively locking said penetration member to said lock/release member; and
    said lock/release member further including an extension member extending toward and over the holding means whereby the movement of said extension by a digit of the user will release the lock/release member from both said insertion tube and said penetration member for slidable movement of said penetration member within said insertion tube.

2. The apparatus for inserting and fixing an IUD to the fundus according to claim 1, wherein said clamping means is a half sleeve which slides over and releasably grips said insertion tube.

3. The apparatus for inserting and fixing an IUD to the fundus according to claim 1, wherein said locking means is a lug for releasable engagement with a corresponding hole in said penetration member.

4. The apparatus for inserting and fixing an IUD to the fundus according to claim 1, wherein said extension projects toward and over the thumb of the user whereby the elevation of the thumb will move said extension to release said lock/release member.

5. The apparatus for inserting and fixing an IUD to the fundus according to claim 1, wherein said insertion tube is made of high-density polyethylene.

6. The apparatus for inserting and fixing an IUD to the fundus according to claim 1, wherein said penetration member is made of acetyl copolymer material.

7. The apparatus for inserting and fixing an IUD to the fundus according to claim 1, wherein said predetermined distance is about one centimeter.

8. The apparatus for inserting and fixing an IUD to the fundus according to claim 1, further comprising:
    a cervical stop means on said insertion tube to limit insertion of said insertion tube to touching contact with the fundus.

9. The apparatus for inserting and fixing an IUD to the fundus according to claim 8, wherein said cervical stop is made of molded thermoplastic rubber.

* * * * *